United States Patent [19]

Neu József et al.

[11] Patent Number: 4,877,893

[45] Date of Patent: Oct. 31, 1989

[54] PROCESS FOR THE PREPARATION OF 2-(O-ALKYL)-2-THIO-1,3,2-OXATHIOPHOSPHOLANES

[75] Inventors: Neu József; Imre Csatlós; András Varga, all of Hódmezövásárhely; Róbert Surányi, Szeged; Zoltán Ilovai; Sándor Gaál, both of Hódmezövásárhely; József Karsai, Velence; Endre Sebestyén, Agárd; Éva Gárdi, Budapest; Károly Siki, Székesfehérvár; István Tóth, Miskolc; Guszt/e,acu/a/ v Gál, Sajóbábony; Zsolt Dombay, Miskolc; Mrs. Erzsébet Grega née Tóth, Miskolc; Csaba Pavliscsák, Sajóbábony; Gyula Tarpai, Miskolc; Péter Bonnyay, Miskolc; Pál Sántha, Miskolc, all of Hungary

[73] Assignee: Eszakmagyarorszagi Vegyimuvek, Sajobabony, Hungary

[21] Appl. No.: 181,778

[22] Filed: Apr. 15, 1988

[30] Foreign Application Priority Data

Apr. 15, 1987 [HU] Hungary .............................. 1650/87

[51] Int. Cl.$^4$ .............................................. C07F 9/21
[52] U.S. Cl. .................................................... 558/86
[58] Field of Search ......................................... 558/86

[56] References Cited

U.S. PATENT DOCUMENTS 3,159,664  12/1964  Bartlett ................................. 558/86

OTHER PUBLICATIONS

Zemlyanskii et al., "Chem. Abstracts," vol. 60, (1964) 10577b.
Eto et al., "Chem. Abstracts", vol. 95, (1981) 95:75384y.

Primary Examiner—Anton H. Sutto
Attorney, Agent, or Firm—Herbert Dubno; Jonathan Myers

[57] ABSTRACT

A fungicidal composition comprising as active ingredient a 2-(O-[substituted]alkyl)-2-thio-1,3,2-oxathiophospholane of the Formula I

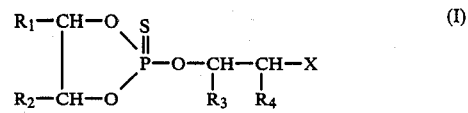

wherein
$R_1, R_2, R_3$ and $R_4$ independently from each other stand for hydrogen, $C_{1-6}$ alkyl, $C_{2-6}$ alkynyl and
X represents halogen, hydrogen, $C_{1-6}$ alkyl or mercapto. The process for the preparation of the compounds of the Formula I involves phosphorous pentasulfide, alcohols and pyridine. The compositions are wide spectrum fungicides, particularly useful in combating Sclerotinia sp., Penicillium sp., Alternaria sp., Fusarium sp., Phytophthora infestans and powdery mildew.

5 Claims, No Drawings

PROCESS FOR THE PREPARATION OF 2-(O-ALKYL)-2-THIO-1,3,2-OXATHIOPHOSPHO-LANES

FIELD OF THE INVENTION

This invention relates to 2-(0-[substituted/alkyl]-2-thio-1,3,2-oxathiophospholane derivatives and a process for the preparation of these compounds.

According to an aspect of the present invention there are provided fungicidal compositions comprising as active ingredient a 2-(0-[substituted/alkyl)-2-thio-1,3,2-oxathio-phospholane derivative of the Formula I

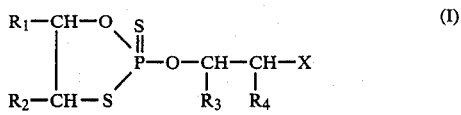

wherein
$R_1$, $R_2$, $R_3$ and $R_4$ each independently of the others stands for hydrogen, $C_{1-6}$ alkyl, $C_{2-6}$ alkenyl or $C_{2-6}$ alkynyl and
X represents halogen, hydrogen, $C_{1-6}$ alkyl or mercapto).

According to a further aspect of the present invention there is provided a process for the preparation of the compounds of the Formula I.

BACKGROUND OF THE INVENTION

In the last twenty years phosphoric acid derivatives have played an important role in plant protection. It appears from the prior art that first place the insecticidal effect of the said components was recognized. The insecticidal and acaricidal effect of phosphoric acid esters was disclosed in Hungarian Patent specifications Nos. 157,085 and 190,843 and also in Hungarian laid-open patent application No. T/34,672. The insecticidal effect of thiophosphoric and -phosphonic acid was described e.g. in Hungarian patent specification No. 188,155 and Hungarian laid-open patent application No. T/37,003, while the insecticidal activity of dithio phosphoric acid derivatives was set forth e.g. in Hungarian patent specifications Nos. 184,742, 186,562 and 186,981.

The fungicidal effect of several phosphine and phosphite derivatives, respectively, was disclosed in Hungarian laid-open patent applications Nos. T/31,985, T/33,356, T/33,374 and T/40,557, while the said activity of phthalimide derivatives was described e.g. in Hungarian patent specification No. 174,708.

In the last five years phosphinate and phosphonate derivatives possessing herbicidal effects have been prepared. Such compounds are disclosed e.g. in Hungarian patent specifications Nos. 184,725, 185,774, 186,422 and 191,363 and also in Hungarian laid-open patent applications Nos. T/31,541, T/33,376 and T/39,335. Hungarian laid-open patent application No. T/39,334 relates to phosphonate derivatives having a plant growth regulating effect.

Phosphoric acid ester derivatives may be of widely varying chemical structure. Several such compounds having insecticidal activity comprise a heterocyclic group. Compounds of this type are disclosed in Hungarian laid-open patent applications Nos. T/39,752, T/39,978, and T/40,448 and further in US patents Nos. 3,317,561 and 3,341,407.

There are further known phosphoric acid ester derivatives in which the phosphorus atom forms part of a 5-7-membered ring comprising three hetero atoms (two oxygen atoms and one phosphorus atom). The said compounds are set forth in US patent specifications No. 3,478,133 and Hungarian laid-open patent application no. T/38,223.

N.I. Zemlianszky and I.V. Muraviev CZhurnal Obshchei Khimii, 34, 1. 89–101, (1964)) on preparing dithiophosphoric acid ester having insecticidal effect and substituted in the B-position of the alkyl radical have found that when the potassium salt of 0,0-di-(β-chloroethyl)-dithio-phosphate is allowed to stand in acetonous solution in a desiccator filled with phosphorous pentoxide, cylization takes place with the precipitation of potassium chloride and a cyclic O,S-ethylene-O-(β-chloroethyl)-thiophosphate is formed. The reaction velocity of the said ring-closure may be inceased by heating the acetonous solution. The authors have not studied further the cyclic compounds and the cited publication has been directed to the preparation of potassium salts of dithiophosphoric acid derivatives and acyl derivatives of dialkyl dithiophosphoric acids.

DESCRIPTION OF THE INVENTION

It has been found that 1,3,2-oxathiophospholane derivatives having wide-spectrum fungicidal activity can be prepared by reacting halogenated alcohols or a halogenated alcohol and an alcohol with phosphorous pentasulfide in a solvent as medium and reacting the dithiophosphoric acid derivative thus obtained with a base, preferably pyridine. This recognition has led to the elaboration of the present invention.

The present invention relates to fungicidal compositions comprising as active ingredient a 2-(0-[substituted-]alkyl)-2-thio-1,3,2-oxathio-phospholane derivative of the Formula I

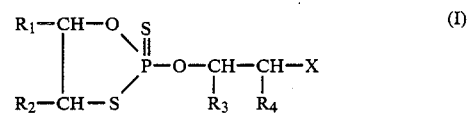

(wherein
$R_1$, $R_2$, $R_3$ and $R_4$ each independently stands for hydrogen, $C_{1-6}$ alkyl, $C_{2-6}$ alkenyl or $C_{2-6}$ alkynyl and
X represents halogen, hydrogen, $C_{1-6}$ alkyl or mercapto in admixture with inert solid or liquid carriers.

The present invention also relates to a process for the preparation of the active ingredients of the Formula I which comprises reacting phosphorous pentasulfide in an organic solvent—preferably anhydrous benzene—at a temperature between 20° C. and 100° C. - preferably elevating the temperature during the reaction—with (substituted) alcohols of the Formulae II

and III

(wherein $R_1$, $R_2$, $R_3$ and $R_4$ are as stated above and Hal stands for chlorine or bromine), thereafter reacting the dithiophosphoric acid derivative of the Formula IV

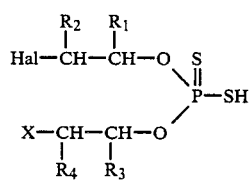

thus obtained with a base—preferably pyridine - at a temperature between 60° C. and 80° C., and finally isolating the 1,3,2-oxathiophospholane derivative of the Formula I by usual cooling, neutralizing, separating, washing, drying and distilling steps and—if necessary—subjecting the product to trans-halogenation by heating to boiling in acetone as medium with an alkali halide.

Preferred representatives of the compounds of the Formula I and physical constants thereof are summarized in Table 1.

TABLE I

| No. | $R_1$ | $R_2$ | $R_3$ | $R_4$ | X | $n_D^{23}$ |
|---|---|---|---|---|---|---|
| 1 | H | H | H | H | Cl | 1.5602 |
| 2 | H | H | H | H | Br | 1.5857 |
| 3 | H | H | H | H | I | 1.5971 |
| 4 | $CH_3$ | H | H | H | Cl | 1.5702 |
| 5 | $CH_3$ | H | H | H | Br | 1.5804 |
| 6 | $CH_3$ | H | H | H | I | 1.5906 |
| 7 | H | $CH_3$ | H | H | Cl | 1.5804 |
| 8 | H | $CH_3$ | H | H | Br | 1.5902 |
| 9 | H | $CH_3$ | H | H | I | 1.5908 |
| 10 | H | H | $CH_3$ | H | Cl | 1.5503 |
| 11 | H | H | $CH_3$ | H | Br | 1.5603 |
| 12 | H | H | $CH_3$ | H | I | 1.5704 |
| 13 | H | H | H | $CH_3$ | Cl | 1.5572 |
| 14 | H | H | H | $CH_3$ | Br | 1.5704 |
| 15 | H | H | H | $CH_3$ | I | 1.5804 |
| 16 | $CH_3$ | $CH_3$ | H | H | Cl | 1.5724 |
| 17 | $CH_3$ | $CH_3$ | H | H | Br | 1.5904 |
| 18 | $CH_3$ | $CH_3$ | H | H | I | 1.5908 |
| 19 | $CH_3$ | H | $CH_3$ | H | Cl | 1.5422 |
| 20 | $CH_3$ | H | $CH_3$ | H | Br | 1.5627 |
| 21 | $CH_3$ | H | $CH_3$ | H | I | 1.5828 |
| 22 | $CH_3$ | H | H | $CH_3$ | Cl | 1.5422 |
| 23 | $CH_3$ | H | H | $CH_3$ | Br | 1.5623 |
| 24 | $CH_3$ | H | H | $CH_3$ | I | 1.5738 |
| 25 | H | $CH_3$ | H | $CH_3$ | Cl | 1.5422 |
| 26 | H | $CH_3$ | H | $CH_3$ | Br | 1.5628 |
| 27 | H | $CH_3$ | H | $CH_3$ | I | 1.5923 |
| 28 | H | H | $CH_3$ | $CH_3$ | Cl | 1.5524 |
| 29 | H | H | $CH_3$ | $CH_3$ | Br | 1.5623 |
| 30 | H | H | $CH_3$ | $CH_3$ | I | 1.5729 |
| 31 | H | $CH_3$ | $CH_3$ | $CH_3$ | Cl | 1.5672 |
| 32 | H | $CH_3$ | $CH_3$ | $CH_3$ | Br | 1.6264 |
| 33 | H | $CH_3$ | $CH_3$ | $CH_3$ | I | 1.5962 |
| 34 | $CH_3$ | $CH_3$ | $CH_3$ | H | Cl | 1.5762 |
| 35 | $CH_3$ | $CH_3$ | $CH_3$ | H | Br | 1.5804 |
| 36 | $CH_3$ | $CH_3$ | $CH_3$ | H | I | 1.5960 |
| 37 | $CH_3$ | H | $CH_3$ | $CH_3$ | Cl | 1.5878 |
| 38 | $CH_3$ | H | $CH_3$ | $CH_3$ | Br | 1.5906 |
| 39 | $CH_3$ | H | $CH_3$ | $CH_3$ | I | 1.5908 |
| 40 | $CH_3$ | $CH_3$ | H | $CH_3$ | Cl | 1.5670 |
| 41 | $CH_3$ | $CH_3$ | H | $CH_3$ | Br | 1.5702 |
| 42 | $CH_3$ | $CH_3$ | H | $CH_3$ | I | 1.5706 |
| 43 | $CH_3$ | $CH_3$ | $CH_3$ | $CH_3$ | Cl | 1.5662 |
| 44 | $CH_3$ | $CH_3$ | $CH_3$ | $CH_3$ | Br | 1.5708 |
| 45 | $CH_3$ | $CH_3$ | $CH_3$ | $CH_3$ | I | 1.5706 |
| 46 | H | H | H | $CH_3$ | H | 1.5529 |
| 47 | $CH_3$ | H | H | $CH_3$ | H | 1.5806 |
| 48 | H | $CH_3$ | H | $CH_3$ | H | 1.5706 |
| 49 | H | H | $CH_3$ | $CH_3$ | H | 1.5604 |
| 50 | H | H | H | $CH_3$ | $CH_3$ | 1.5448 |
| 51 | H | $C_2H_5$ | H | $CH_3$ | H | 1.5253 |
| 52 | $CH_3$ | H | H | $CH_3$ | $CH_3$ | 1.5224 |

TABLE I-continued

| No. | $R_1$ | $R_2$ | $R_3$ | $R_4$ | X | $n_D^{23}$ |
|---|---|---|---|---|---|---|
| 53 | $CH_3$ | $CH_3$ | $CH_3$ | $CH_3$ | H | 1.5352 |
| 54 | $CH_3$ | $CH_3$ | $CH_3$ | $CH_3$ | $CH_3$ | 1.5352 |
| 55 | H | H | H | H | H | 1.5529 |
| 56 | H | H | H | H | SH | 1.5572 |
| 57 | H | H | $CH_3$ | H | H | 1.5369 |
| 58 | H | H | H | H | $C_2H_5$ | 1.5352 |
| 59 | H | H | H | $C_2H_5$ | H | 1.5539 |
| 60 | $CH_3$ | H | H | $C_2H_5$ | H | 1.5816 |
| 61 | H | $CH_3$ | H | H | $C_2H_5$ | 1.5726 |
| 62 | H | H | $CH_3$ | $C_2H_5$ | H | 1.5614 |
| 63 | $CH_3$ | $CH_3$ | H | H | $C_2H_5$ | 1.5252 |
| 64 | $CH_3$ | H | H | $C_2H_5$ | H | 1.5234 |
| 65 | $CH_3$ | $CH_3$ | $CH_3$ | $C_3H_7$ | H | 1.5362 |
| 66 | $CH_3$ | $CH_3$ | $CH_3$ | $C_2H_5$ | H | 1.5372 |
| 67 | H | H | H | i-$C_3H_7$ | H | 1.5518 |

Further details of the compounds of the Formula I are to be found in the following Examples without limiting the scope of protection to the said Examples.

EXAMPLE 1

To a mixture of 0.1 mole (22.2 g) of phosphorous pentasulfide and 25 ml of anhydrous benzene at 45°–50° C. 26.8 ml (32.2 g, 0.4 mole) of 2-chloroethanol are added under vigorous stirring, whereupon the reaction mixture is stirred at 78°–80° C. for 7–9 hours. During this period of time the phosphorous pentasulfide completely reacts. The reaction mixture is diluted with 40 ml of benzene and a mixture of 0.2 g (16 ml) of pyridine and 16 ml of benzene is added dropwise within about 15 minutes. The reaction mixture is stirred at 70° C. for an hour, cooled and poured into 200 ml of 5% icecold hydrochloric acid. The layers are separated, the organic phase is washed neutral in succession with water, an icecold 10% sodium carbonate solution and water, pre-dried with saturated sodium-chloride, dried over sodiumsulfate and the solvent is removed in vacuo at a temperature of about 60° C./about 100 Torr. Thus 2-(O-2'-chloroethyl)-2-thio-1,3,2-oxathiophospholane is obtained, (Compound 1 of Table I), yield: 82%.

Active ingredient content (gas chromatography): 97.5%.

EXAMPLE 2

One proceeds according to Example 1 except that 0.4 mole of 2-chloroethanol is replaced by 0.4 mole of 2-bromoethanol. Thus 2-(O-2'-bromoethyl)-2-thio-1,3,2-oxathiophospholane is obtained (compound No. 2 of Table I), yield: 76%.

Active ingredient content: 96%.

EXAMPLE 3

A mixture of 2.18 g (0.01 mole) of 2-(O-2'-chloroethyl)-2-thio-1,3,2-oxathiophospholane, 2.75 g (0.015 mole) of sodium iodide and 20 ml of acetone is refluxed for 4 hours, whereupon the acetone is removed in vacuo. The residue is partitioned between 20 ml of ether and 20 ml water. The two layers are separated, the organic phase is washed with 20 ml of a 1% sodium sulfite solution and water and finally evaporated. Thus 2-(O-2'-iodoethyl)-2-thio1,3,2-oxathiophospholane is obtained, (Compound No. 3 of Table I, yield: 60%.

Active ingredient content: 85%.

EXAMPLE 4

To a mixture of 0.1 mole of phosphorous pentasulfide and 25 ml of anhydrous benzene at 45°–50° C. a mixture of 0.2 mole of I-bromo-2-propanol and 0.2 mole of 2-chloroethanol is added within 60 minutes under vigorous stirring. The temperature is raised to 75° C. and the reaction is carried out for 4–5 hours. The benzene solution of the mixed phosphoric acid ester is diluted with benzene to the double-fold volume and 0.2 mole of pyridine is added dropwise. The reaction is stirred at 60°–80° C. for half an hour, cooled and poured into 200 ml of icecold 5% hydrochloric acid. The organic layer is washed in succession with water, a 5% icecold sodium carbonate solution, water and a saturated sodium chloride solution, dried over sodium sulfate and evaporated in vacuo. 2-(0-2'-chloroethyl)-2-thio-5-methyl-1,3,2-oxathiophospholane is obtained (Compound No. 4 of Table I), yield: 78%.

Active ingredient content: 96%.

EXAMPLE 5

2-(0-2'-chloroethyl)-2-thio-5-methyl-1,3,2-oxathiophospholane (Compound No. 7 of Table I), is prepared by reacting 0.1 mole of phosphorous pentasulfide, 0.2 mole of 2-bromo-1-propanol and 0.2 mole of 2-chloroethanol in an analogous manner to Example 4. Cyclization is carried out by adding 0.2 mole of pyridine. Yield: 82%.

Active ingredient content: 97%.

EXAMPLE 6

2-(0-1'-methyl-2'-chloroethyl)-2-thio-1,3,2-oxathiophospholane (Compound No. 10 of Table I) is prepared by reacting 0.1 mole of phosphorous pentasulfide, 0.2 mole of 1-chloro-2-propanol and 0.2 mole of 2-bromoethanol in an analogous manner to Example 4. C Ring closure is carried out by adding 0.2 mole of pyridine. Yield: 75%.

Active ingredient content: 92%.

EXAMPLE 7

2-(0-2'-methyl-2'-chloroethyl)-2-thio-1,3,2-oxathiophospholane (Compound No. 13 of Table I) is prepared by reacting 0.1 mole of phosphorous pentasulfide, 0.2 mole of 2-chloro-1-propanol and 0.2 mole 2-bromoethanol in analogous manner to Example 4. Ring closure is carried out by adding 0.2 mole of pyridine. Yield: 81%.

Active ingredient content: 93%.

EXAMPLE 8

2-(0-2'-chloroethyl)-2-thio-4,5-dimethyl-1,3,2-oxathiophospholane (Compound No. 16 of TableI) is prepared by reacting 0.1 mole of phosphorous pentasulfide, 0.2 mole of 2-bromo-3-butanol and 0.2 mole of 2-chloroethanol in analogous manner to Example 4. Ring closure is carried out by adding 0.2 mole of pyridine. Yield: 68%.

Active ingredient content: 92%.

EXAMPLE 9

2-(0-1'-methyl-2'-chloroethyl)-2-thio-5-methyl-1,3,2-oxathiophospholane (Compound No. 19 of Table I) is prepared by reacting 0.1 mole of phosphorous pentasulfide, 0.2 mole of 1-bromo-2-propanol and 0.2 mole of 1-chloro-2-propanol in an analogous manner to Example 4. Ring-closure is carried out by adding 0.2 mole of pyridine. Yield: 65%.

Activbe ingredient content: 95%.

EXAMPLE 10

2-(0-2'-methyl-2'-chloroethyl)-2-thio-5-methyl-1,3,2-oxathiophospholane (Compound No. 22 of Table I) is prepared by reacting 0.1 mole of phosporous pentasulfide, 0.2 mole of 1-bromo-2-propanol and 0.2 mole of 2-chloro-1-propanol in an analogous manner to Example 4. Ring closure is accomplished by adding 0.2 mole of pyridine. Yield: 73%.

Active ingredient content: 97%.

EXAMPLE 11

2-(0-1'-methyl-2'-chloroethyl)-2-thio-4,5-dimethyl-1,3,2-oxathiophospholane (Compound No. 34 of Table I) is prepared by reacting 0.1 mole of phosphorous pentasulfide, 0.2 mole of 2-bromo-3-butanol and 0.2 moles of 1-chloro-2-propanol in an analogous manner to Example 4. Ring-closure is accomplished by adding 0.2 mole of pyridine. Yield: 67%.

Active ingredient content: 90%.

EXAMPLE 12

2-(0-1',2'-dimethyl-2'-chloroethyl)-2-thio-4,5-dimethyl-1,3,2-oxathiophospholane (Compound No. 43 of Table I) is prepared by reacting 0.1 mole of phosphorous pentasulfide, 0.2 mole of 2-bromo-3-butanol and 0.2 moles of 2-chloro-3-butanol in an analogous manner to Example 4. Ringclosure is accomplished by adding 0.2 mole of pyridine. Yield: 61%.

Active ingredient content: 91%.

EXAMPLE 13

2-(0-n-propyl)-2-thio-1,3,2-oxathiophospholane (Compound No. 46 of Table I) can be prepared by reacting 0.1 mole of phosphorous pentasulfide, 0.2 mole of 2-bromoethanol and 0.2 mole of n-propanol in an analogous manner to Example 4. Ring-closure is accomplished by adding 0.2 mole of pyridine. Yield: 79%.

Active ingredient content: 95%.

EXAMPLE 14

2-(0-n-propyl)-2-thio-5-methyl-1,3,2-oxathiophospholane (Compound No. 47 of Table I) can be prepared by reacting 0.1 mole of phosphorous pentasulfide, 0.2 mole of 1-bromo-2-propanol and 0.2 mole of n-propanol in an analogous manner to Example 4. Ring-closure is accomplished by adding 0.2 mole of pyridine. Yield: 75%.

Active ingredient content: 92%.

EXAMPLE 15

2-(0-n-propyl)-2-thio-4-methyl-1,3,2-oxathiophospholane (Compound No. 48 of Table I) can be prepared by reacting 0.1 mole of phosphorous pentasulfide, 0.2 mole of 2-bromo-1-propanol and 0.2 mole of n-propanol in an analogous manner to Example 4. Ring-closure is accomplished by adding 0.2 mole of pyridine. Yield: 73%.

Active ingredient content: 95%.

EXAMPLE 16

2-((0-1'-methyl-n-propyl)-2-thio-1,3,2-oxathiophospholane (Compound No. 49 of Table I) can be prepared by reacting 0.1 mole of phosphorous pentasulfide, 0.2 mole of 2-bromoethanol and 0.2 mole of 2-butanol in an analogous manner to Example 4. Ring closure is accomplished by adding 0.2 mole of pyridine. Yield: 81%.

Active ingredient content: 98%.

EXAMPLE 17

2-(0-2'-methyl-n-propyl)-2-thio-1,3,2-oxathiophospholane (Compound No. 50 of Table I) can be prepared by reacting 0.1 mole of phosphorous pentasulfide, 0.2 mole of 2-bromoethanol and 0.2 mole of 2-methyl-1-propanol in an analogous manner to Example 4. Ring closure is accomplished by adding 0.2 mole of pyridine. Yield: 80%.

Active ingredient content: 95%.

EXAMPLE 18

2-(0-n-propyl)-2-thio-4-ethyl-1,3,2-oxathiophospholane (Compound No. 51 of Table I) is prepared by reacting 0.1 mole of phosphorous pentasulfide, 0.2 mole of 2-bromo-1-butanol and 0.2 mole of 2-methyl-1-propanol in an analogous [manner to Example 4. Ring closure is accomplished by][adding 0.2 mole of pyridine. Yield: 80%.]

Active ingredient content: 95%.

EXAMPLE 19

2-(0-2'-methyl-n-propyl)-2-thio-5-methyl-1,3,2-oxathiophospholane (Compound No. 52 of Table I) may be prepared by reacting 0.1 mole of phosphorous pentasulfide, 0.2 mole of 1-bromo-2-propanol and 0.2 mole of 2-methyl-1-propanol in an analogous manner to Example 4. Ring closure is accomplished by adding 0.2 mole of pyridine. Yield: 81%.

Active ingredient content: 93%.

EXAMPLE 20

2-(0-1'-methyl-n-propyl)-2-thio-4,5-dimethyl1,3,2-oxathiophospholane (Compound No. 53 of Table I) may be prepared by reacting 0.1 mole of phosphorous pentasulfide, 0.2 mole of 2-bromo-3-butanol and 0.2 mole of 2-n-butaanol in an analogous manner to Example 4. Ring closure is accomplished by adding 0.2 mole of pyridine. Yield: 75%.

Active ingredient content: 90%.

EXAMPLE 21

2-(0-1',2'-dimethyl-n-propyl)-2-thio-4,5-dimethyl1,3,2-oxathiophospholane (Compound No. 54 of Table I) may be prepared by reacting 0.1 mole of phosphorous pentasulfide, 0.2 mole of 2-bromo-3-butanol and 0.2 mole of 3-methyl-2-butanol in an analogous manner to Example 4. Ring closure is accomplished by adding 0.2 mole of pyridine. Yield: 70%.

Active ingredient content: 88%.

EXAMPLE 22

2-(0-n-butyl)-2-thio-1,3,2-oxathiophospholane (Compound No. 59 of Table I) may be prepared by reacting 0.1 mole of phosphorous pentasulfide, 0.2 mole of 2-bromoethanol and 0.2 mole of n-butanol in an analogous manner to Example 4. Ring closure is accomplished by adding 0.2 mole of pyridine. Yield: 80%.

Active ingredient content: 96%.

EXAMPLE 23

2-(0-n-butyl)-2-thio-5-methyl-1,3,2-oxathiophospholane (Compound No. 60 of Table I) may be prepared by reacting 0.1 mole of phosphorous pentasulfide, 0.2 mole of 1-bromo-2-propanol and 0.2 mole of n-butanol in an analogous manner to Example 4. Ring closure is accomplished by adding 0.2 mole of pyridine. Yield: 78%.

Active ingredient content: 95%.

EXAMPLE 24

2-(0-n-butyl)-2-thio-4-methyl-1,3,2-oxathiophospholane (Compound No. 61 of Table I) may be prepared by reacting 0.1 mole of phosphorous pentasulfide, 0.2 mole of 2-bromo-1-propanol and 0.2 mole of n-butanol in an analogous manner to Example 4. Ring closure is accomplished by adding 0.2 mole of pyridine. Yield: 76%.

Active ingredient content: 95%.

EXAMPLE 2-(0-1'-methyl-n-butyl)-2-thio-1,3,2-oxathiophospholane (Compound No. 62 of Table I) may be prepared by reacting 0.1 mole of phosphorous pentasulfide, 0.2 mole of2-bromoethanol and 0.2 mole of secondary amylalcohol in an analogous manner to Example 4. Ring closure is accomplished by adding 0.2 mole of pyridine. Yield: 83%.

Active ingredient content: 98%.

EXAMPLE 26

2-(0-n-butyl)-2-thio-4,5-dimethyl-1,3,2-oxathiophospholane (Compound No. 63 of Table I) may be prepared by reacting 0.1 mole of phosphorous pentasulfide, 0.2 mole of 2-bromo-3-butanol and 0.2 mole of n-butanol in an analogous manner to Example 4. Ring closure is accomplished by adding 0.2 mole of pyridine. Yield: 81%.

Active ingredient content: 93%.

The active ingredients thus obtained are formulated before use by means of suitable methods and by adding suitable additives into spray, dusting powder and granule formulations. The preparation of the fungicidal compositions of the present invention may be illustrated by the following Examples without limiting the scope of protection to the said Examples.

EXAMPLE 27

Emulsifiable concentrate (20 EC)

20% by weight of 2-(0-2'-chloroethyl)-2-thio-1,3,2-oxathiophospholane (Compound No. 1 of Table I) are admixed with 5% by weight of alkyl phenyl polyethyleneglycol ether and 5% by weight of alkyl polyglycol ether emulsifiers.

After complete admixture 70% by weight of xylene are added. The active ingredient content of the composition being readily emulsifiable in water amounts to 20%.

In the preparation of the above compositions any compound of the Formula I can be used as active ingredient.

EXAMPLE 28

Emulsifiable concentrate (80 EC)

80% by weight of 2-(0-2'-bromoethyl)-2-thio-1,3,2-oxathiophospholane (Compound No. 2 of Table I) are admixed with 5% by weight of polyethylene glycol oleate (Emulsogen EL) emulsifier and the mixture is diluted to 100 % with xylene).

Thus an emulsifiable concentrate having an active ingredient content of 80% by weight is obtained.

EXAMPLE 29

Emulsifiable concentrate (60 EC)

60% by weight of 2-(0-1'-methyl-2'-iodoethyl)-2-thio-5-methyl-1,3,2-oxathiophospholane (Compound No. 21 of Table I) are admixed with 5% by weight of polyethyleneglycol having a degree of polymerization of 1000 (Carbowax 1000) and 10% by weight of an addition product of ethylene oxide formed with di(isohexyl-isoheptyl) phenol (emulsifiers). The mixture is diluted to 100% with benzene. The active ingredient content of the emulsifiable concentrate thus obtained amounts to 60% by weight.

EXAMPLE 30

Emulsifiable concentrate (1 EC)

2% by weight of calcium dodecyl benzenesulfonate dispersing agent are dissolved in 97% by weight of benzene, whereupon 1% by weight of 2-(0-2'-iodoethyl)-2-thio-4-methyl-1,3,2-oxathiophospholane (Compound No. 9 of Table I) is added dropwise under vigorous stirring. Thus an emulsifiable concentrate having an active ingredient content of 1% by weight is obtained.

EXAMPLE 31

Wettable powder (50 WP)

50% by weight of 2-(0-n-propyl)-2-thio-1,3,2-oxathiophospholane (Compound No. 46 of Table I), 9% by weight of sodium-calcium-lignosulfonate dispersing agent, 1% by weight of isobutyl naphthyl sulfonate wetting agent and 40% by weight of freshly precipitated and acid-free washed Kieselguhr are ground in a suitable mill at a temperature below 30° C. Thus a wettable powder having an active ingredient content of 50% by weight and showing good adhesion properties is obtained.

EXAMPLE 32

Dusting powder composition

5% by weight of 2-(0-n-propyl)-2-thio-4-ethyl-1,3,2-oxathiophospholane (Compound No. 51 of Table I), 2% by weight of isobutyl naphthyl sulfonate wetting agent and 93% by weight of Kieselguhr (siliceous earth) are ground in a suitable mill under cooling to particle size of 20 microns. Thus a dusting powder composition having an active ingredient content of 5% by weight is obtained.

EXAMPLE 33

Soil disinfectant granules

10% by weight of 2-(0-1',2'-dimethyl-n-propyl)-2-thio-4,5-dimethyl-1,3,2-oxathiophospholane (Compound No. 54 of Table I), 90% by weight of precipitated clay, 5% by weight of calcium carbonate and 4% by weight of paraffine oil are admixed, whereupon the mixture is granulated to granules having a diameter of 2 mm by such an amount of water that the mixture can be easily formed. The granules are dried in a drier equipped with a rotating drum. The active ingredient content of the granules thus obtained amount to 10% by weight.

EXAMPLE 34

Soil disinfectant granules

10% by weight of 2-(0-n-propyl)-2-thio-5-methyl1,3,2-oxathiophospholane (Compound No. 47 of Table I) are admixed with 90% by weight of China-clay and such an amount of water is added that the mixture can be easily granulated. The granules are dried in a drier equipped with a rotating drum at 30°-40° C. The active ingredient content of the granules thus obtained is 10% by weight.

The fungicidal activity of the compositions according to the present invention is tested on six fungi species (Sclerotinia sp., Penicullium sp., Alternaria spp., Fusarium sp., Pytophthora infestans, Erysihpe graminis) according to various modes of application (spray, dressing agent, soil treatment) and compared to that of known fungicidal agents (Aliette, Mancozeb, Benonyl Tilt). The tests used and the results obtained are summarized in the following Examples. In the Table and number of the active ingredients used corresponds to that appearing in Table I.

EXAMPLE 35

Fungicidal effect against Sclerotinia sclerotinia

Agar nutrient media (Diameter 70 MM, thickness 10 mm) infected by Sclerotonia sclerotinia suspension are treated with 20 EC formulations prepared according to Example 27 and comprising 1, 10, 100 and 1000 ppm, respectively of the active ingredient of the Formula I. The fungicidal effect of the compositions is evaluated on the 3rd day after treatment by measuring the diameter of the Fungi colonies.

The results are summarized in Table II.

TABLE II

| Test compound | Diameter of colony (mm) | | | |
|---|---|---|---|---|
| | 1 ppm | 10 ppm | 100 ppm | 1000 ppm |
| Untreated control | 41.7 | | | |
| 1 | 39.4 | 31.7 | 3.5 | 0 |
| 2 | 32.9 | 29.3 | 3.1 | 0 |
| 3 | 37.4 | 30.0 | 2.1 | 0 |
| 4 | 34.6 | 27.6 | 0 | 0 |
| 5 | 35.4 | 29.2 | 1.7 | 0 |
| 6 | 39.3 | 30.0 | 1.0 | 0 |
| 7 | 38.1 | 31.2 | 0 | 0 |
| 8 | 37.6 | 29.9 | 1.0 | 0 |
| 9 | 39.2 | 27.6 | 3.9 | 0 |
| 10 | 40.1 | 31.3 | 1.8 | 0 |
| 11 | 34.6 | 30.6 | 2.8 | 0 |
| 12 | 35.9 | 27.4 | 3.7 | 0 |
| 13 | 33.9 | 32.1 | 1.7 | 0 |
| 14 | 38.1 | 28.1 | 0 | 0 |
| 15 | 34.3 | 30.3 | 1.4 | 0 |
| 16 | 39.4 | 27.6 | 1.7 | 0 |
| 17 | 40.1 | 30.2 | 1.0 | 0 |
| 18 | 38.2 | 28.0 | 1.5 | 0 |
| 19 | 36.5 | 27.4 | 3.9 | 0 |
| 20 | 34.9 | 28.2 | 1.6 | 0 |
| 21 | 33.8 | 25.8 | 2.50 | 0 |
| 22 | 37.8 | 30.1 | 2.9 | 0 |
| 23 | 36.9 | 29.7 | 3.6 | 0 |
| 24 | 38.1 | 29.0 | 3.2 | 0 |
| 25 | 38.8 | 30.3 | 1.0 | 0 |
| 26 | 40.9 | 32.1 | 1.6 | 0 |
| 27 | 41.2 | 28.6 | 1.4 | 0 |
| 28 | 33.6 | 27.4 | 0 | 0 |
| 29 | 31.9 | 25.2 | 1.2 | 0 |
| 30 | 34.8 | 30.0 | 0 | 0 |
| 31 | 37.4 | 29.2 | 4.0 | 0 |
| 32 | 38.9 | 30.0 | 3.2 | 0 |
| 33 | 33.2 | 26.4 | 0 | 0 |
| 34 | 34.6 | 23.9 | 1.3 | 0 |
| 35 | 38.1 | 25.7 | 2.6 | 0 |
| 36 | 37.2 | 26.9 | 0 | 0 |
| 37 | 39.2 | 27.1 | 0 | 0 |
| 38 | 37.8 | 31.3 | 0 | 0 |
| 39 | 37.2 | 30.2 | 3.6 | 0 |
| 40 | 34.9 | 28.0 | 1.9 | 0 |
| 41 | 37.6 | 30.0 | 2.6 | 0 |
| 42 | 38.2 | 31.2 | 3.5 | 0 |
| 43 | 37.6 | 28.2 | 2.4 | 0 |
| 44 | 35.4 | 28.1 | 4.0 | 0 |
| 45 | 39.2 | 30.0 | 1.6 | 0 |

TABLE II-continued

| Test compound | Diameter of colony (mm) | | | |
|---|---|---|---|---|
| | 1 ppm | 10 ppm | 100 ppm | 1000 ppm |
| 46 | 34.6 | 28.7 | 4.2 | 0 |
| 47 | 33.9 | 30.2 | 3.9 | 0 |
| 48 | 35.8 | 29.1 | 2.8 | 0 |
| 49 | 37.2 | 30.4 | 4.0 | 0 |
| 50 | 36.5 | 29.7 | 3.7 | 0 |
| 51 | 34.3 | 30.0 | 3.2 | 0 |
| 52 | 37.1 | 28.6 | 3.0 | 0 |
| 53 | 35.8 | 30.0 | 3.8 | 0 |
| 54 | 34.9 | 29.0 | 4.1 | 0 |
| 55 | 33.1 | 28.2 | 0 | 0 |
| 56 | 40.2 | 31.5 | 1.2 | 0 |
| 57 | 37.8 | 25.9 | 0 | 0 |
| 58 | 36.2 | 29.1 | 1.9 | 0 |
| 59 | 34.3 | 28.5 | 4.0 | 0 |
| 60 | 33.7 | 30.0 | 3.8 | 0 |
| 61 | 35.6 | 28.9 | 2.7 | 0 |
| 62 | 37.0 | 30.2 | 3.9 | 0 |
| 63 | 34.2 | 29.9 | 3.1 | 0 |
| 64 | 36.9 | 28.7 | 3.0 | 0 |
| 65 | 35.8 | 30.1 | 3.7 | 0 |
| 66 | 34.8 | 28.8 | 4.0 | 0 |
| 67 | 36.3 | 29.6 | 3.6 | 0 |

It appears from the above data that in a dose of 100 ppm from the 67 test compounds 11 compounds exhibit a complete fungicidal effect against Sclerotinia sclerotinia, while in a dose of 1000 ppm all the test compounds of the Formula I show a 100% fungicidal activity.

EXAMPLE 36

Fungicidal effect against Penicullium cyclopium

The series of measureents described in Example 35 is carried out except that the agar nutrient media are infected by a Penicillium cyclopium Fungi strain and the test is evaluated on the 7th day after treatment. The results are disclosed in Table III.

TABLE III

| Test compound | Diameter of colony (mm) | | | |
|---|---|---|---|---|
| | 1 ppm | 10 ppm | 100 ppm | 1000 ppm |
| Untreated treated | 26.5 | | | |
| 1 | 23.2 | 20.0 | 8.0 | *0 |
| 2 | 24.6 | 19.0 | 8.4 | 0 |
| 3 | 25.0 | 18.6 | 7.1 | 0 |
| 4 | 24.1 | 19.4 | 9.0 | 0 |
| 5 | 20.1 | 19.5 | 7.8 | 0 |
| 6 | 21.3 | 17.3 | 9.0 | 0 |
| 7 | 25.4 | 16.7 | 8.8 | 0 |
| 8 | 20.0 | 18.3 | 7.9 | 0 |
| 9 | 23.2 | 15.8 | 5.7 | 0 |
| 10 | 21.3 | 19.0 | 6.8 | 0 |
| 11 | 24.1 | 17.5 | 8.3 | 0 |
| 12 | 25.8 | 16.1 | 4.7 | 0 |
| 13 | 24.5 | 19.2 | 7.5 | 0 |
| 14 | 18.2 | 17.6 | 7.9 | 0 |
| 15 | 19.1 | 15.5 | 5.8 | 0 |
| 16 | 23.2 | 18.1 | 6.6 | 0 |
| 17 | 24.9 | 14.2 | 8.9 | 0 |
| 18 | 25.2 | 14.2 | 6.3 | 0 |
| 19 | 21.5 | 15.6 | 5.5 | 0 |
| 20 | 20.1 | 17.7 | 4.1 | 0 |
| 21 | 23.7 | 20.0 | 6.9 | 0 |
| 22 | 24.6 | 16.2 | 6.7 | 0 |
| 23 | 22.6 | 15.8 | 4.3 | 0 |
| 24 | 24.2 | 15.0 | 5.9 | 0 |
| 25 | 26.0 | 19.8 | 7.8 | 0 |
| 26 | 20.5 | 18.8 | 8.5 | 0 |
| 27 | 23.8 | 17.5 | 4.6 | 0 |
| 28 | 18.2 | 14.7 | 5.7 | 0 |
| 29 | 25.0 | 19.2 | 8.0 | 0 |
| 30 | 21.2 | 20.0 | 7.2 | 0 |

TABLE III-continued

| Test compound | Diameter of colony (mm) | | | |
|---|---|---|---|---|
| | 1 ppm | 10 ppm | 100 ppm | 1000 ppm |
| 31 | 23.6 | 14.9 | 9.0 | 0 |
| 32 | 19.4 | 16.7 | 7.2 | 0 |
| 33 | 22.3 | 20.7 | 6.1 | 0 |
| 34 | 19.7 | 16.5 | 4.9 | 0 |
| 35 | 25.1 | 14.7 | 8.3 | 0 |
| 36 | 23.2 | 16.8 | 7.2 | 0 |
| 37 | 19.9 | 17.5 | 6.6 | 0 |
| 38 | 24.3 | 18.6 | 7.4 | 0 |
| 39 | 21.1 | 15.8 | 4.7 | 0 |
| 40 | 18.9 | 20.0 | 6.8 | 0 |
| 41 | 24.1 | 16.4 | 4.9 | 0 |
| 42 | 22.2 | 17.2 | 7.5 | 0 |
| 43 | 25.2 | 18.4 | 6.3 | 0 |
| 44 | 17.9 | 17.1 | 5.1 | 0 |
| 45 | 24.2 | 15.5 | 6.0 | 0 |
| 46 | 25.1 | 18.9 | 7.9 | 0 |
| 47 | 23.8 | 20.1 | 8.3 | 0 |
| 48 | 24.2 | 19.2 | 8.5 | 0 |
| 49 | 26.3 | 20.3 | 7.5 | 0 |
| 50 | 25.1 | 19.2 | 7.7 | 0 |
| 51 | 24.9 | 18.7 | 8.2 | 0 |
| 52 | 26.2 | 20.0 | 8.8 | 0 |
| 53 | 24.8 | 19.2 | 7.6 | 0 |
| 54 | 25.2 | 18.8 | 7.9 | 0 |
| 55 | 21.9 | 18.1 | 8.0 | 0 |
| 56 | 24.6 | 18.1 | 8.8 | 0 |
| 57 | 18.7 | 20.0 | 6.2 | 0 |
| 58 | 21.9 | 16.1 | 8.4 | 0 |
| 59 | 25.0 | 18.7 | 7.6 | 0 |
| 60 | 23.6 | 19.9 | 8.2 | 0 |
| 61 | 24.0 | 19.0 | 8.3 | 0 |
| 62 | 26.1 | 20.2 | 7.4 | 0 |
| 63 | 24.8 | 18.5 | 8.5 | 0 |
| 64 | 26.0 | 20.0 | 8.7 | 0 |
| 65 | 24.6 | 19.1 | 7.5 | 0 |
| 66 | 25.0 | 18.6 | 7.5 | 0 |
| 67 | 25.1 | 19.3 | 7.0 | 0 |

The data of Table III clearly show that the compounds of the Formula I exhibit in a dose of 100 ppm a very significant and in a dose of 1000 ppm a complete fungicidal effect against Penicillium cyclopium, irrespective of the substituent definition of the compound of the Formula I used.

EXAMPLE 37

Fungicidal effect against Alternaria tenuis

The series of measurements according to Example 35 is carried out except that the agar nutrient media are infected by Alternaria Tenius and evaluation is accomplished on the 5th day after treatment. The results obtained are summarized in Table IV.

TABLE IV

| Test compound | Diameter of colony (mm) | | | |
|---|---|---|---|---|
| | 1 ppm | 10 ppm | 100 ppm | 1000 ppm |
| Untreated control | 36.8 | | | |
| 1 | 33.5 | 25.8 | 7.6 | 0 |
| 2 | 30.9 | 26.1 | 5.3 | 0 |
| 3 | 34.6 | 22.4 | 6.8 | 0 |
| 4 | 32.6 | 23.7 | 6.5 | 0 |
| 5 | 34.9 | 22.3 | 7.9 | 0 |
| 6 | 35.5 | 21.0 | 6.0 | 0 |
| 7 | 34.7 | 25.5 | 5.9 | 0 |
| 8 | 30.1 | 26.1 | 6.4 | 0 |
| 9 | 30.6 | 24.6 | 8.9 | 0 |
| 10 | 33.9 | 21.6 | 5.8 | 0 |
| 11 | 35.9 | 24.1 | 4.6 | 0 |
| 12 | 34.5 | 22.0 | 4.8 | 0 |
| 13 | 32.2 | 25.8 | 5.1 | 0 |
| 14 | 31.3 | 21.3 | 5.7 | 0 |
| 15 | 35.9 | 21.1 | 5.5 | 0 |

TABLE IV-continued

| Test compound | Diameter of colony (mm) | | | |
|---|---|---|---|---|
| | 1 ppm | 10 ppm | 100 ppm | 1000 ppm |
| 16 | 34.4 | 22.0 | 6.3 | 0 |
| 17 | 33.2 | 23.9 | 5.6 | 0 |
| 18 | 35.8 | 22.8 | 5.3 | 0 |
| 19 | 32.3 | 21.7 | 4.3 | 0 |
| 20 | 33.2 | 25.0 | 5.0 | 0 |
| 21 | 30.9 | 24.2 | 7.2 | 0 |
| 22 | 34.4 | 26.1 | 8.7 | 0 |
| 23 | 33.8 | 24.1 | 5.2 | 0 |
| 24 | 34.8 | 25.5 | 6.1 | 0 |
| 25 | 33.8 | 24.0 | 6.5 | 0 |
| 26 | 34.2 | 21.1 | 6.2 | 0 |
| 27 | 33.5 | 22.4 | 8.8 | 0 |
| 28 | 34.2 | 22.4 | 4.8 | 0 |
| 29 | 33.2 | 23.6 | 6.5 | 0 |
| 30 | 30.1 | 26.7 | 7.2 | 0 |
| 31 | 36.0 | 23.6 | 8.1 | 0 |
| 32 | 31.2 | 27.4 | 7.2 | 0 |
| 33 | 33.0 | 21.3 | 6.3 | 0 |
| 34 | 30.3 | 25.9 | 5.7 | 0 |
| 35 | 34.7 | 27.1 | 6.2 | 0 |
| 36 | 32.5 | 20.7 | 4.3 | 0 |
| 37 | 30.8 | 21.9 | 5.6 | 0 |
| 38 | 30.2 | 24.5 | 6.9 | 0 |
| 39 | 34.6 | 23.3 | 7.3 | 0 |
| 40 | 31.3 | 21.7 | 6.1 | 0 |
| 41 | 33.8 | 25.1 | 7.3 | 0 |
| 42 | 32.1 | 20.4 | 9.0 | 0 |
| 43 | 32.4 | 23.3 | 6.2 | 0 |
| 44 | 33.5 | 26.2 | 7.0 | 0 |
| 45 | 34.0 | 20.4 | 5.7 | 0 |
| 46 | 34.2 | 24.3 | 5.8 | 0 |
| 47 | 33.5 | 25.7 | 7.0 | 0 |
| 48 | 36.1 | 24.6 | 6.3 | 0 |
| 49 | 34.3 | 25.9 | 7.0 | 0 |
| 50 | 35.2 | 23.8 | 5.3 | 0 |
| 51 | 35.1 | 24.3 | 6.9 | 0 |
| 52 | 34.8 | 26.2 | 4.7 | 0 |
| 53 | 33.9 | 25.4 | 6.6 | 0 |
| 54 | 34.7 | 24.6 | 7.2 | 0 |
| 55 | 32.4 | 23.5 | 5.2 | 0 |
| 56 | 32.8 | 22.1 | 6.0 | 0 |
| 57 | 31.7 | 26.0 | 7.1 | 0 |
| 58 | 32.7 | 23.9 | 7.5 | 0 |
| 59 | 34.0 | 24.1 | 5.6 | 0 |
| 60 | 33.3 | 25.5 | 6.8 | 0 |
| 61 | 36.2 | 24.3 | 6.2 | 0 |
| 62 | 34.1 | 25.7 | 6.9 | 0 |
| 63 | 35.0 | 24.2 | 6.7 | 0 |
| 64 | 34.6 | 26.1 | 4.5 | 0 |
| 65 | 33.8 | 25.3 | 6.6 | 0 |
| 66 | 34.5 | 24.4 | 7.0 | 0 |
| 67 | 35.4 | 23.8 | 5.3 | 0 |

It can be clearly seen from Table IV that the active ingredients of the Formula I show in a dose of 100 ppm a very significant and in a dose of 1000 ppm a complete fungicidal effect against Alternaria tenuis. The fungicidal activity of the individual active ingredients is practically independent of the character of the halogeno and alkyl substituents of the Formula I.

EXAMPLE 38

Determination of fungicidal effect on paprika seeds

The test is carried out on paprika seeds placed on agar nutrient medium and impregnated with phytopathogenic Fungi (Alternaria sp., Penicillium sp., Sclerotinia sp.). The paprika seeds are treated with various doses of 2-(0-2'-chloroethyl)-2-thio-1,3,2-oxathiophospholane (Compound No. 1 of Table I) and the known fungicidal agent Aliette, respectively.

(1) Untreated control
(2) Compound No. 1    1 ppm
(3) Compound No. 1    5 ppm
(4) Compound No. 1    10 ppm
(5) Compound No. 1    50 ppm
(6) Compound No. 1    100 ppm
(7) Compound No. 1    1000 ppm
(8) Aliette    1 ppm
(9) Aliette    5 ppm
(10) Aliette    10 ppm
(11) Aliette    50 ppm
(12) Aliette    100 ppm
(13) Aliette    1000 ppm Aliette = aluminum-tris-(O-ethyl-phosphate).

The concentration data relate to the active ingredient. Treatment is carried out by using a 20 EC prepared according to Example 27. Evaluation is carried out on the 5th day after treatment by measuring the diameter of the Fungi colonies. The average results of the 8 replicates, each are summarized in Table V.

TABLE V

| Treatment | Diameter of Colony (MM) | | |
|---|---|---|---|
| No. | Sclerotinia | Alternaria | Penicillium |
| 1 | 41.50 | 36.62 | 23.35 |
| 2 | 39.37 | 33.50 | 22.20 |
| 3 | 40.62 | 32.25 | 20.05 |
| 4 | 31.75 | 25.87 | 20.05 |
| 5 | 10.62 | 16.75 | 19.40 |
| 6 | 3.50 | 7.62 | 8.12 |
| 7 | 0 | 0 | 0 |
| 8 | 40.45 | 34.05 | 21.35 |
| 9 | 39.64 | 35.16 | 20.66 |
| 10 | 36.44 | 29.41 | 18.45 |
| 11 | 28.06 | 26.13 | 17.63 |
| 12 | 22.40 | 19.16 | 16.62 |
| 13 | 6.75 | 8.92 | 10.15 |

The above data show that the fungicidal activity of the compositions of the present invention is superior to that of the well known and widespreadly used agent Aliette against all of the three fungal strains used. The surplus effect is particularly significant at an active ingredient dose range of 100 and 1000 ppm whereby the composition according to the present invention gives a significantly better result and exhibits even a 100% fungicidal effect. The known composition Aliette exerts in a dose of 1000 ppm a weaker effect than the composition of the present invention when applied in a dose of 100 ppm.

EXAMPLE 39

Testing of fungicidal effect when used as seed dressing agents

In this test cotton, maize, sunflower and sugar beet seeds strongly infected by pathogens and treated with different doses of 2-(0-2'-chloroethyl)-2-thio-1,3,2-oxathiophospholane (Compound No. 1) are used. The doses amount to 50, 100 and 200 g of active ingredient, respectively. As reference seeds being either untreated or treated with Mancozeb (manganese +zinc/-ethylene bis-dithiocarbamte) 0.8 kg/t +Benomyl (1-butyl carbamoyl-benzimidazole-2-methylcarbamate) 0.5 kg/t are used.

Compound No. 1 of the present invention is formulated as 50 WP in an analogous manner to Example 31. The test is carried out in six replicates, by sowing 10 seeds in each replicate. The results are evaluated by determining the shoot up % related to the control. The results thus obtained are summarized in Table VI (average).

TABLE VI

| Treatment | Shoot up % | | | |
|---|---|---|---|---|
| | Cotton | Maize | Sunflower | Sugar beet |
| Untreated control | 100 | 100 | 100 | 100 |
| Compound No. 1 50 g/t | 146 | 121 | 132 | 205 |
| Compound No. 1 100 g/t | 218 | 133 | 154 | 312 |
| Compound No. 1 200 g/t | 255 | 125 | 129 | 156 |
| Mankoceb 0.8 kg/to + Benomyl 0.5 kg/to | 116 | 108 | 125 | 107 |

It appears from the data of Table VI that the composition of the present invention when applied in significantly lower doses exhibits a much higher fungicidal effect than the well-known combination used for the same purpose.

EXAMPLE 40

Testing of fungicidal effect when used for soil disinfection

The soil is watered and admixed with a Fusarium sp. and Alternaria sp. suspension. In the infected soil cotton and sugar beet seeds are sown, namely 10 seeds per replicate. Eight replicates are used in the test. The soil is treated with 2-(0-2'-chloroethyl)-2-thio-1,3,2-oxathiophospholane (Compound No. 1) in a dose of 1 kg of active ingredient.ha⁻1. Treatment is carried out with soil disinfectant granules prepared in an analogous manner to Example 33. Evaluation is carried out by determining the shoot up % related to the untreated control. The results (average) are summarized in Table VII.

TABLE VII

| Treatment | Shoot up % | |
|---|---|---|
| | Cotton | Sugar beet |
| Untreated Control | 100 | 100 |
| Compound No. 1 | 239 | 346 |

The above data show that the composition of the present invention exhibits a very strong fungicidal effect through the soil.

EXAMPLE 41

Testing of fungicidal effect against Phytophthora infestans, on tomato leaf

From a 60 EC composition comprising as active ingredient 60% by weight of 2-(0-2'-chloroethyl)-2-thiol,3,2-oxathiophospholane (Compound No. 1) and formulated in an analogous manner to Example 29 a dilution series of 0, 0.01, 0.1, 1.0, 10, 100 and 1000 ppm, respectively is prepared, and 12 ml of each dilution is applied onto wet filter paper pieces in Petridishes having a diameter of 100 mm. The Petridishes are placed into a refrigerator for an hour. From the tomato leaves discs are cut out with the aid of a 15 mm cork drill and in each Petri-dishe 5 discs are put on the filter paper. A spore suspension of Phytophthora infestans pathogen is applied in a volume of 100 ul in each disc onto the surface of the leaves by using a micropipette (spore concentration 50,000/ml). The Petridishes are incubated at 15°-18° C.for 7 days whereupon the infectedness of the leaf discs and the fungicidal effect of the different doses of the composition are determined. The results are summarized in Table VIII.

TABLE VIII

| Composition | Dose ppm | No. of deaf discs infected by Phytophthora infestans | | Fungicidal activity % |
|---|---|---|---|---|
| | | No. | % | |
| Compound No. 1 60 EC | 0 | 5 | 100 | 0 |
| Compound No. 1 60 EC | 0.01 | 5 | 100 | 0 |
| Compound No. 1 60 EC | 0.1 | 5 | 100 | 0 |
| Compound No. 1 60 EC | 1.0 | 4 | 80 | 20 |
| Compound No. 1 60 EC | 10 | 0 | 0 | 100 |
| Compound No. 1 60 EC | 100 | 0 | 0 | 100 |
| Compound No. 1 60 EC | 1000 | 0 | 0 | 100 |

The above data show that the composition of the present invention provided in a dose of 10–1000 ppm a complete protection against Phytophthora infestans on tomato leaves.

EXAMPLE 42

Testing of fungicidal effect against powdery mildew in winter wheat

In a glass house in pots having a diameter of 12 cm winter wheat plants artificially infected by Erysiphe graminis (powdery mildew) are culticated. At a height stage of 20 cm the plants are treated with a composition formulated in an analogous manner to Example 28 and comprising 80% by weight of 2-(0-2'-chloroethyl)-2-thio-1,3,2-thiophospholane (Compound No. 1) at a dose of 0.5 and 1.0 kg.ha⁻1, respectively; the volume of the spray amounts to 110 1.ha⁻1. As control untreated plants and also plants treated with Tilt 250 EC (25% of propiconazol =1-[2-(2,4-dichlorophenyl)-4-propyl-1,3-dioxolane-2-yl-methyl]-1H-1,2,4-triazole) in a dose of 0.5 and 1.0 1.ha⁻¹, respectively, are used. Evaluations are carried out in each case on the 7th day after spraying by calculating the infectedness index according to the following scale:

0 = free of symptoms
1 = infectedness of 5%
2 = infectedness of 6–10%
3 = infectedness of 11–25%
4 = infectedness of 26–50%
5 = infectedness of 51–75%
6 = infectedness of 76–100%.

The above infectedness / values represent the ratio of the healthy and infected leaf surface area, and the average coverage by mycelia of the leaf surface belonging to four leaf stages. From the above data the infectedness index ($F_i$) is calculated by the following equation:

$$F_i = \frac{a_1 \cdot f_i}{n}$$

$a_1$ = infectedness value according to the above scale;
$f_i$ = frequency belonging to the individual scale values;
n = No. of tested plants.

The results of four replicates are summarized in Table IX.

TABLE IX

| Treatment | Dose (a.i.) | Powdery mildew infectedness ($F_j$) | | | | |
|---|---|---|---|---|---|---|
| | | I | II | III | IV | Average |
| Untreated control | — | 4.00 | 4.50 | 4.77 | 4.66 | 4.48 |
| Compound No. 1 80 EC | 0.5 kg/ha | 2.50 | 2.20 | 1.77 | 1.82 | 2.07 |
| Compound No. 1 80 EC | 1.0 kg/ha | 1.00 | 0.38 | 0.56 | 0.71 | 0.66 |
| Tilt 250 EC | 0.5 l/ha | 1.11 | 1.10 | 1.20 | 1.33 | 1.19 |

TABLE IX-continued

| Treatment | Dose (a.i.) | Powdery mildew infectedness (Fi) | | | | |
|---|---|---|---|---|---|---|
| | | I | II | III | IV | Average |
| Tilt 250 EC | 1.0 l/ha | 1.15 | 1.10 | 1.20 | 1.30 | 1.18 |

The data of the above Table prove that the compositions of the present invention combats powdery mildew in a dose of 1.0 kg a.i.ha$^{-1}$ more efficiently than the well-known and widespreadly used composition Tilt 250 EC in the same dose. On decreasing the dose of the active ingredients to 0.5 kg/ha, Tilt 250 EC shows a better result but it must be taken into consideration that in this dose the lower effect of the composition of the present invention is accompanied by a wider spectrum of effect.

Tilt 250 EC and the other agents used against powdery mildew are ineffective against e.g. Phytophthora sp., while on the other hand the compositions of the present invention may be succesfully used against the said important pathogen group as well.

EXAMPLE 43

Testing of fungicidal effect against germination diseases in winter wheat and maize The tests are accomplished on 20 m² plots in four replicates on field "chernozem" (black soil). The soil is first pre-sown with soya whereupon winter wheat (type MV-9) is sown.

The amount of seed-corn is 250 kg.ha$^{-1}$. The pathogenic infectedness of dressed seeds and the percentual germination is evaluated on Papavizas selective nutrient medium and by incubation in a moist chamber, respectively, by using 200 seed-corns for each treatment.

In a field experiment in 2-4 leaves' stage phenophase the shoot up plants are counted on 5×1 running meters and the height of the plants is measured.

In maize the test is carried out on 0.1 ha plots in two replicates by using a Pi 3732 hybride. The corns are sown in rows of 76×19 cm. Evaluation is accomplished in an angle and two-leaves stage, respectively. Germination and Fusarium spp. infectedness percentage is determined in laboratory on 200 seeds.

From the invention compounds 2-(0-2'-chloroethyl)-2-thio-1,3,2-thiophospholane (Compound No. 1) is used in the form of a composition having an active ingredient content of 80% by weight and formulated in an analogous manner to Example 28. As reference agent Ortocid 50 WP (N-trichloromethylthio-tetrahydro-phthalimide) is used.

tion are combating efficiently Fusarium infection of seeds already in very low doses (0.1–0.2 kg/a.i.) without causing any damage to the seed-corns.

EXAMPLE 44

Testing of fungicidal effect against Rhizoctonia solani on potato

The test is carried out on 50 m² plots in four replicates on Desirie potato species. The seed tubers are sown after dressing in an amount of 3.0 t.ha$^{-1}$. The infectedness of the shoots is determined on the 50th day after sowing on 100 shoots per plot on the basis of a scale between 0 and 6 by counting the infectedness index, while the rate of infectedness of the tubers is calculated on 200 tubers and the crop of the plots is evaluated on harvesting.

From the compounds of the present invention 2-(0-1'-methyl-2'-chloroethyl)-2-thio-1,3,2-oxathiophospholane (Compound No. 6) is used in the form of a composition having an active ingredient content of 50% by weight and formulated in an analogous manner to Example 31. As reference agent Rhizolex 25 FL (2,6-dichloro-p-tolyl-0,0-dimethylphosphorothiolate) is used.

TABLE XI

| Treatment | Dose kg·l/ha | Degree of infectedness | | | Crop kg/50 m² |
|---|---|---|---|---|---|
| | | Shoot F % | Fi | Tuber F % | |
| Control | — | 13.5 | 0.19 | 15.8 | 96.6 |
| Compound No. 6 50 WP | 0.5 | 3.75 | 0.08 | 1.75 | 105.4 |
| Compound No. 6 50 WP | 1.0 | 1.50 | 0.04 | 1.00 | 121.3 |
| Compound No. 6 50 WP | 2.0 | 1.05 | 0.02 | 0.50 | 125.2 |
| Rhizolex 25 FL | 0.8 | 1.50 | 0.02 | 0.50 | 116.5 |

Fi = infectedness index; ratio of healthy and infected surface area, wherein 0 = free of infectedness ... 6 = infectedness of 76–100%.

On dressing the seed-roots with the compositions of the present invention the compositions of the present invention the Rhyzoctonia infectedness of both the shoots and the tubers is reduced.

The decrease of infectedness results in an increase in crop growth.

EXAMPLE 45

Testing of fungicidal effect against Alternaria solani Alternaria (leaf blight) and Septoria lycopersici (Septoria leaf blight) on tomato The test is carried out in two replicates on 140 m² plots on tomato (Peto species).

TABLE X

| Treatments | Dose l.kg/t | wheat | | | | Shot plants No./20 m | | | |
|---|---|---|---|---|---|---|---|---|---|
| | | Winter No./m | plant height cm | Germination % | Fusarium spp. F % | angle stage | two leaves stage | Germination % | Fusarium spp. F % |
| Control | | 58.3 | 6.3 | 90.5 | 24.5 | 84.6 | 106.1 | 94.5 | 14.5 |
| Compound No. 1 80 EC | | 66.8 | 7.9 | 94.0 | 6.0 | 88.9 | 112.3 | 99.5 | 5.0 |
| Compound No. 1 80 EC | | 70.5 | 7.6 | 97.0 | 1.5 | 96.3 | 115.8 | 103.5 | 0.5 |
| Compound No. 1 80 EC | | 62.1 | 7.0 | 92.5 | 0.0 | 89.5 | 109.8 | 100.5 | 0.0 |
| Compound No. 1 80 EC | | 56.9 | 6.5 | 89.5 | 0.0 | 88.8 | 109.7 | 97.5 | 0.0 |
| Ortocid 50 WP | 2.00 | 68.2 | 6.9 | 92.5 | 5.5 | 85.3 | 107.2 | 100.0 | 4.5 |

Field experiments carried out in winter wheat and maize prove that the compositions of the present inven- Treatments are begun after the appearance of the first symptoms, and are repeated three times. The degree of infectedness is determined before the 4th treatment (A) and on the 12th day (B) on each plot on the basis of the bonity of 10×20 randomly selected plants with the aid of a scale between 0 and 6.

From the invention compounds (2-(0-n-propyl)-2-thio-4-ethyl-1,3,2-oxathiopholane (Compound No. 51) is used in the form of a composition having an active ingredient content of 5% by weight and formulated in an analogous manner to Example 32. As reference agent Cineb 80 WP (zinc ethylene bis dithiocarbamate) is used.

TABLE XII

| Treatment | Dose kg/ha | Infectedness index | | | |
|---|---|---|---|---|---|
| | | Alternaria solani | | Septoria Lycopersici | |
| | | A | B | A | B |
| Control | — | 2.75 | 3.58 | 0.33 | 0.56 |
| Composition of Example 32 | 10.0 | 1.59 | 1.66 | 0.09 | 0.11 |
| Composition of Example 32 | 20.0 | 1.00 | 1.16 | 0.09 | 0.10 |
| Composition of Example 32 | 40.0 | 0.84 | 0.95 | 0.03 | 0.05 |
| Cineb 80 WP | 2.0 | 1.52 | 1.71 | 0.08 | 0.11 |

Infectedness index = ratio of healthy and infected surface area, wherein 0 = free of infectedness ... 6 = infectedness of 76–100%.

Thus the active ingredients of the present invention when used in the form of a dusting composition are suitable for effective inhibition of the growht of fungal diseases on tomato.

EXAMPLE 46

Fungicidal effect against Erysiphe graminis f. sp. tritici (wheat powdery mildew) and Fusarium spp. (Fusariosis) on winter wheat The test is carried out on 20 m² plots in four replicates on winter wheat. The first treatment is carried out on shooting up and the second is accomplished on flowering. Powdery mildew infectedness is evaluated before the second treatment (A) and 15 days later (B) by observing 100 productive shoots for each leaf stage per plot. The results are expressed with the aid of the scale between 0 and 6 by calculating the infectedness index. Activity against ear fusariosis is evaluated on the basis of the ratio of the ears showing symptoms which are found at the stage of complete ripeness on 5×1 m² samples per plot. On harvesting the drop is weighed, from average samples the weight of 1000 corns is determined and on a Papavizas' nutrient medium the internal Fusarium spp. infectedness of the corn is measured.

From the compounds of the present invention 2-(0-2'-chloroethyl)-2-thio-1,3,2-oxathiopholane (Compound No. 1) is used in the form of a composition having an active ingredient content of 20% by weight and formulated in an analogous manner to Example 27. As reference agent Sulphur 800 FW (800 g.l[1] of sulfur) and Dithane M 45 (zinc manganese ethylene bis dithiocarbamate) are used.

TABLE XIII

| Treatments | Dose kg · l/ha | Powdery mildew Fi | | Fusarium F % | | Crop t/ha | Weight of 1000 corns g |
|---|---|---|---|---|---|---|---|
| | | A | B | ear | corn | | |
| Control | — | 1.01 | 1.93 | 6.6 | 17.8 | 5.09 | 46.2 |
| Composition of Example 27 20 EC | 1.25 | 0.95 | 1.77 | 5.9 | 14.1 | 5.24 | 46.8 |
| Composition of Example 27 20 EC | 2.50 | 0.68 | 1.02 | 5.0 | 7.6 | 5.39 | 47.2 |
| Composition of Example 27 20 EC | 5.00 | 0.54 | 0.89 | 4.2 | 7.1 | 5.50 | 47.1 |
| Sulphur 800 FW + Dithane M-45 | 5.0 + 2.0 | 0.66 | 1.09 | 4.7 | 8.0 | 5.52 | 47.3 |

Fi = infectedness index ratio of healthy infected surface area, wherein 0 = free of infectedness ... 6 = infectedness of 76–100%.

The composition of the present invention reduces powdery mildew and ear Fusariosis diseases of winter wheat to a significant extent. The biological activity of the composition of the present invention is in a dose of 0.5–1.0 kg of active ingredient/ha approximately the same as the effect of the contact fungicides generally used in combating the said diseases.

EXAMPLE 47

Testing of fungicidal effect against germination diseases on pea

The test is carried out on 5 m² plots in four replicates on brown forest soil by using seed-corn of the Jubileum species. In field experiments the shoot up and infected (ill) plants are counted when the first foliageleaves appear (A) and 15 days later (B) on each plot. Laboratory evaluation is carried out by determining the infectedness of 200 seed-corns after 10 days' incubation in a moist chamber. From the invention compounds 2-(O-1'-methyl-n-butyl)-2-thio-1,3,2-oxathiopholane (Compound No. 62) is used in the form of a composition having an active ingredient content of 50% by weight and formulated in an analogous manner to Example 31. As reference agent Orthocid 50 WP (N-trichloro-methylthio-tetrahydro-phthalimide) is used.

TABLE XIV

| Treatments | Dose kg/t | Number of plants | | | | | | | |
|---|---|---|---|---|---|---|---|---|---|
| | | Shoot up | | | | ill | | | |
| | | A | | B | | A | | B | |
| | | No./plot | % | No./plot | % | No./plot | % | No./plot | % |
| Control | — | 148.5 | 100 | 148.8 | 100 | 0.5 | 100 | 0.5 | 100 |
| Compound No. 62 50 WP | 0.5 | 165.5 | 111.4 | 166.5 | 111.9 | 0.0 | 0.0 | 0.0 | 0.0 |
| Compound No. 62 50 WP | 1.0 | 170.5 | | 172.5 | | 0.0 | 0.0 | 0.0 | 0.0 |
| Compound No. 62 50 WP | 2.0 | 172.5 | | 176.5 | | 0.0 | 0.0 | 0.0 | 0.0 |
| Orthocid 50 WP | 2.0 | 165.5 | 111.4 | 168.8 | 113,4 | 0,0 | 0.0 | 0.0 | 0.0 |

TABLE XV

| Treatments | Dose kg/t | Seed infectedness, % | | | | | |
|---|---|---|---|---|---|---|---|
| | | Fusarium spp. | Acohyta spp. | Rhizoctonia spp. | Alternaria spp. | Rhizopus spp. | Penicillium spp. |
| Control | — | 47.5 | 1.5 | 1.8 | 13.5 | 3.5 | 9.0 |
| Compound No. 62 50 WP | 0.5 | 4.5 | 2.0 | 0.5 | 2.5 | 0.5 | 3.0 |
| Compound No. 62 50 WP | 1.0 | 2.0 | 0.0 | 0.0 | 0.0 | 0.5 | 0.0 |
| Compound No. 62 50 WP | 2.0 | 0.5 | 0.0 | 0.0 | 0.0 | 0.0 | 0.0 |
| Orthocid 50 WP | 2.0 | 2.5 | 0.0 | 1.0 | 0.0 | 0.0 | 0.0 |

The compositions of the present invention can be efficiently used against germination diseases of pea. This statement is supported by observations relating to the improvement of the germination percentage and the death of pathogens.

EXAMPLE 48

Testing of fungicidal effect against Botrytis cinerea (grey rot) on grape

Test is carried out on 60 m² plots in four replicates on Gloria Hungariae species grape sown in rows of 3x1 m and cordon cultivated. Treatments are carried out as from the beginning of the blossoming of grape each 10th-14th day six times. The results are evaluated by means of the bonity 4×50 bunches per plot, with the aid of a scale between 0 and 4 by determining the infectedness index.

Evaluations are carried out in the middle of July (A), in August (B) and in September (C).

From the compounds of the present invention 2-(O-n-butyl)-2-thio-5-methyl-1,3,2-oxathiophospholane (Compound No. 60) is used in the form of a composition having an active ingredient content of 50% by weight and formulated in an analogous manner to Example 29. As reference agent Orthocid 50 WP (N-trichloro-methylthio-tetrahydro-phthalimide) is used.

TABLE XVI

| Treatments | Dose 1 kg/ha | Infectedness index of | | |
|---|---|---|---|---|
| | | A | B | C |
| Control | — | 0.41 | 0.39 | 0.45 |
| Compound No. 60 50 EC | 0.5 | 0.32 | 0.29 | 0.35 |
| Compound No. 60 50 EC | 1.0 | 0.30 | 0.30 | 0.31 |
| Compound No. 60 50 EC | 2.0 | 0.21 | 0.17 | 0.22 |
| Orthocid 50 WP | 2.0 | 0.35 | 0.29 | 0.38 |

Botrytis cinerea can be efficiently combated on grape with the compositions of the present invention. The activity of the invention compositions is superior to that of the known agent Orthocid 50 WP generally used in combating Botrytis cinerea.

What we claim is,

1. A process for the preparation of a compound of the Formula (I)

$$\begin{array}{c} R_1-CH-O \\ | \quad\quad\quad\quad \searrow \overset{S}{\underset{\|}{P}}-O-CH-CH-X \\ R_2-CH-S \nearrow \quad\quad\quad | \quad\quad | \\ \quad\quad\quad\quad\quad\quad\quad\quad R_3 \quad R_4 \end{array} \quad (I)$$

wherein
$R_1$, $R_2$, $R_3$, and $R_4$ independently from each other stand for hydrogen, $C_1$ to $C_6$ alkyl $C_2$ to $C_6$ alkenyl or $C_2$ to $C_6$ alkynyl; and
X is hydrogen, halogen, $C_1$ to $C_6$ alkyl, or mercapto; which comprises the steps of:
(a) reacting phosphorous pentasulfide in an organic solvent at a temperature between 20° C. and 100° C. with a compound of the Formula (II)

$$\begin{array}{c} R_1-CH-OH \\ | \\ R_2-CH-Hal \end{array} \quad (II)$$

and a compound of the Formula (III)

$$\begin{array}{c} R_3-CH-OH \\ | \\ R_4-CH-X \end{array} \quad (III)$$

wherein
Hal is chlorine or bromine, to obtain a compound of the Formula (IV)

$$\begin{array}{c} R_2 \quad R_1 \\ | \quad\quad | \\ Hal-CH-CH-O \searrow \overset{S}{\underset{\|}{P}}-SH \\ X-CH-CH-O \nearrow \\ | \quad\quad | \\ R_4 \quad R_3 \end{array} \quad (IV)$$

(b) treating the compound of the Formula (IV) with a base at a temperature between 60° C. and 80° C. to obtain a compound of the Formula (I); and
(c) isolating the compound of the Formula (I).

2. The process defined in claim 1 wherien according to step (b) the base is pyridine.

3. The process defined in claim 1 wherein according to step (a) the organic solvent is anhydrous benzene.

4. The process defined in claim 1 wherein according to step (a) the temperature is elevated during the course of the reaction.

5. The process defined in claim 1 further comprising the step of trans-halogenating a compound of the Formula (I) wherein X is halogen, following step (c), by heating the compound to boiling in acetone with an alkali halide where the halide is the anion of a different halogen from X.

* * * * *